(12) United States Patent
Huelskamp et al.

(10) Patent No.: US 7,908,334 B2
(45) Date of Patent: Mar. 15, 2011

(54) SYSTEM AND METHOD FOR ADDRESSING IMPLANTABLE DEVICES

(75) Inventors: Paul J. Huelskamp, St. Paul, MN (US); Michael J. Timmons, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 796 days.

(21) Appl. No.: 11/781,107

(22) Filed: Jul. 20, 2007

(65) Prior Publication Data

US 2008/0021972 A1 Jan. 24, 2008

Related U.S. Application Data

(60) Provisional application No. 60/820,059, filed on Jul. 21, 2006, provisional application No. 60/820,050, filed on Jul. 21, 2006.

(51) Int. Cl.
*G06F 15/16* (2006.01)

(52) U.S. Cl. ........ 709/208; 709/202; 709/211; 709/218; 709/248; 600/325; 600/327; 600/332; 600/339; 600/341

(58) Field of Classification Search .................. 709/202, 709/208, 211, 218, 248; 600/325, 327, 332, 600/339, 341, 372, 377, 423, 486
See application file for complete search history.

(56) References Cited

U.S. PATENT DOCUMENTS

| | | | |
|---|---|---|---|
| 3,672,352 A | 6/1972 | Summers | |
| 4,361,153 A | 11/1982 | Slocum et al. | |
| 4,373,527 A | 2/1983 | Fischell | |
| 4,481,950 A | 11/1984 | Duggan | |
| 4,519,401 A | 5/1985 | Ko et al. | |
| 4,573,994 A | 3/1986 | Fischell et al. | |
| 4,614,192 A | 9/1986 | Imran et al. | |
| 4,616,640 A | 10/1986 | Kaali et al. | |
| 4,651,740 A | 3/1987 | Schroeppel | |
| 4,793,825 A | 12/1988 | Benjamin et al. | |
| 5,113,859 A | 5/1992 | Funke | |
| 5,423,334 A | 6/1995 | Jordan | |
| 5,778,882 A * | 7/1998 | Raymond et al. ............. | 600/513 |
| 5,800,478 A | 9/1998 | Chen et al. | |

(Continued)

FOREIGN PATENT DOCUMENTS

EP 0300552 1/1989

(Continued)

OTHER PUBLICATIONS

International Search Report and Written Opinion of international application No. PCT/US2007/074020, mailed Feb. 20, 2008, 15 pp.

(Continued)

*Primary Examiner* — Phuoc Nguyen
(74) *Attorney, Agent, or Firm* — Faegre & Benson LLP

(57) ABSTRACT

A system includes multiple slave devices implanted in a human body, wherein each slave device includes a communication module operable to receive transmitted communications and is associated with a permanent device identifier. The system further includes a master device including a communications module operable to address a first communication to a selected slave device using the permanent device identifier associated with the selected slave device, wherein the first communication includes a local identifier assigned to the selected slave device, the assigned local identifier does not match any other local identifier assigned to any other slave device implanted in the human body, and subsequent communications are addressed to the selected slave device using the assigned local identifier.

15 Claims, 7 Drawing Sheets

U.S. PATENT DOCUMENTS

| | | |
|---|---|---|
| 5,814,089 A | 9/1998 | Stokes et al. |
| 5,833,603 A | 11/1998 | Kovacs et al. |
| 6,140,740 A | 10/2000 | Porat et al. |
| 6,141,588 A | 10/2000 | Cox et al. |
| 6,162,238 A | 12/2000 | Kaplan et al. |
| 6,164,284 A | 12/2000 | Schulman et al. |
| 6,170,488 B1 | 1/2001 | Spillman, Jr. et al. |
| 6,185,452 B1 | 2/2001 | Schulman et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,277,078 B1 | 8/2001 | Porat et al. |
| 6,308,099 B1 | 10/2001 | Fox et al. |
| 6,336,903 B1 | 1/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,431,175 B1 | 8/2002 | Penner et al. |
| 6,440,066 B1 | 8/2002 | Bardy |
| 6,442,413 B1 | 8/2002 | Silver |
| 6,442,433 B1 | 8/2002 | Linberg |
| 6,445,953 B1 | 9/2002 | Bulkes et al. |
| 6,456,883 B1 | 9/2002 | Torgerson et al. |
| 6,472,991 B1 | 10/2002 | Schulman et al. |
| 6,628,989 B1 | 9/2003 | Penner et al. |
| 6,654,638 B1 | 11/2003 | Sweeney |
| 6,675,049 B2 | 1/2004 | Thompson et al. |
| 6,764,446 B2 | 7/2004 | Wolinsky et al. |
| 6,792,311 B2 | 9/2004 | Fox et al. |
| 6,823,031 B1 | 11/2004 | Tatem, Jr. |
| 6,840,956 B1 | 1/2005 | Wolinsky et al. |
| 6,978,182 B2 | 12/2005 | Mazar et al. |
| 6,985,773 B2 | 1/2006 | Von Arx et al. |
| 7,003,350 B2 | 2/2006 | Denker et al. |
| 7,024,248 B2 | 4/2006 | Penner et al. |
| 7,027,871 B2 | 4/2006 | Burnes et al. |
| 7,187,979 B2 | 3/2007 | Haubrich et al. |
| 7,198,603 B2 | 4/2007 | Penner et al. |
| 7,273,454 B2 * | 9/2007 | Raymond et al. ............. 600/301 |
| 7,273,457 B2 | 9/2007 | Penner |
| 2001/0043514 A1 * | 11/2001 | Kita ............... 368/281 |
| 2002/0042561 A1 | 4/2002 | Schulman et al. |
| 2002/0045812 A1 | 4/2002 | Ben-Haim et al. |
| 2002/0065540 A1 | 5/2002 | Lebel et al. |
| 2002/0077553 A1 | 6/2002 | Govari et al. |
| 2002/0077556 A1 | 6/2002 | Schwartz |
| 2002/0128546 A1 | 9/2002 | Silver |
| 2002/0138009 A1 | 9/2002 | Brockway et al. |
| 2002/0151770 A1 | 10/2002 | Noll, III et al. |
| 2002/0183628 A1 | 12/2002 | Reich et al. |
| 2002/0183791 A1 | 12/2002 | Denker et al. |
| 2003/0009093 A1 | 1/2003 | Silver |
| 2003/0009204 A1 | 1/2003 | Amundson |
| 2003/0076082 A1 | 4/2003 | Morgan et al. |
| 2003/0100839 A1 | 5/2003 | Cohen et al. |
| 2003/0125613 A1 | 7/2003 | Enegren et al. |
| 2003/0136417 A1 | 7/2003 | Fonseca et al. |
| 2003/0139677 A1 | 7/2003 | Fonseca et al. |
| 2003/0158584 A1 | 8/2003 | Cates et al. |
| 2003/0181794 A1 | 9/2003 | Rini et al. |
| 2003/0189488 A1 | 10/2003 | Forcier et al. |
| 2003/0191383 A1 | 10/2003 | Ben-Haim et al. |
| 2004/0057340 A1 * | 3/2004 | Charles-Erickson et al. .. 368/10 |
| 2004/0064133 A1 | 4/2004 | Miller et al. |
| 2004/0088009 A1 | 5/2004 | Degroot |
| 2004/0152999 A1 | 8/2004 | Cohen et al. |
| 2004/0199059 A1 | 10/2004 | Brauker et al. |
| 2004/0199238 A1 | 10/2004 | Brown et al. |
| 2005/0015014 A1 | 1/2005 | Fonseca et al. |
| 2005/0056539 A1 | 3/2005 | Morgan et al. |
| 2005/0080346 A1 | 4/2005 | Gianchandani et al. |
| 2005/0159789 A1 | 7/2005 | Brockway et al. |
| 2005/0187482 A1 | 8/2005 | O'Brien et al. |
| 2005/0215887 A1 | 9/2005 | Ben-Haim et al. |
| 2005/0242479 A1 | 11/2005 | Petisce et al. |
| 2006/0004263 A1 * | 1/2006 | Feliss et al. ................. 600/300 |
| 2006/0009818 A1 | 1/2006 | Von Arx et al. |
| 2006/0030903 A1 | 2/2006 | Seeberger et al. |
| 2006/0031378 A1 | 2/2006 | Vallapureddy et al. |
| 2006/0058588 A1 | 3/2006 | Zdeblick |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0136004 A1 | 6/2006 | Cowan et al. |
| 2007/0142728 A1 | 6/2007 | Penner et al. |
| 2008/0021333 A1 | 1/2008 | Huelskamp |
| 2008/0114224 A1 | 5/2008 | Brandy et al. |
| 2008/0129457 A1 * | 6/2008 | Ritter et al. ................. 340/10.1 |
| 2009/0075687 A1 * | 3/2009 | Hino et al. ................... 455/517 |

FOREIGN PATENT DOCUMENTS

| | | |
|---|---|---|
| WO | WO99/34453 | 7/1999 |
| WO | WO99/34731 | 7/1999 |
| WO | WO2004/089465 | 10/2004 |
| WO | 2006045073 A1 | 4/2006 |
| WO | 2006045074 A2 | 4/2006 |
| WO | 2006045075 A1 | 4/2006 |
| WO | 2006069215 A2 | 6/2006 |
| WO | WO2007/070794 | 6/2007 |
| WO | WO2008/011592 | 1/2008 |
| WO | WO2008/011593 | 1/2008 |
| WO | 2009102640 A1 | 8/2009 |

OTHER PUBLICATIONS

International Search Report and Written Opinion of international application No. PCT/US2007/074021, mailed Feb. 25, 2008, 14 pp.

* cited by examiner

SYSTEM AND METHOD FOR ADDRESSING IMPLANTABLE DEVICES

CROSS-REFERENCE TO RELATED APPLICATIONS

This application claims priority to U.S. Provisional Patent Application Ser. No. 60/820,059, entitled "System and Method for Addressing Implantable Devices," and to U.S. Provisional Patent Application Ser. No. 60/820,050, entitled "Multiple Sensor Deployment," both of which were filed on Jul. 21, 2006 and are incorporated herein by reference in their entirety for all purposes.

TECHNICAL FIELD

The present invention relates generally to communication between implantable medical devices. More specifically, the present invention relates to a system and method for addressing implantable medical devices.

BACKGROUND

Medical devices can be implanted in the bodies of patients for various purposes. Some medical devices detect physiologic events and may apply therapy in response to certain events of interest. For example, a cardiac pacemaker can detect a lull in the beating of the patient's heart and apply an electrical pulse to stimulate the heart into beating again. Other devices may be implanted, such as defibrillators, neurostimulators, ICDs, CRTS, drug pumps, and various types of sensors. It is becoming more common to implant multiple devices in a single patient. In such situations, a controller device can communicate with the implanted medical devices. The medical devices can communicate data to the controller in response to commands from the controller. When multiple medical devices are implanted, the controller must be able to direct commands to a selected device with a relatively high degree of reliability.

Conventionally, globally unique identifiers, such as device manufacturing serial numbers, have been used to identify an implanted electronic device during communication with diagnostic and control equipment outside a patient's body. Typical systems involve a single external master controlling communication with a single slave device within the body. Multiple devices within a body in communication with each other or with an external device require using globally unique identifiers as well, but this can unnecessarily burden the local communication traffic.

The representation, in bits, of a globally unique identifier must be sufficiently large to identify a global population of devices. For example, 20- to 64-bit globally unique identifiers are common for electronic devices. In a local patient environment that can consist of approximately 6 implanted devices in communication with each other or with a local device external to the body, transferring large, unique identifiers during communication sessions represents communication overhead that consumes power and delays transfer of desired data within the local environment.

SUMMARY

Embodiments described herein include systems and methods for communicating with an implanted medical device without use of the device's globally unique identifier. For each medical device, a shorter local device identifier is selected and used for addressing the device, in order to reduce overhead in communications. The local identifier is unique within a single patient's body, but not necessarily globally unique among identifiers of devices outside the patient's body. The number of devices in any single body will be considerably smaller than a global population of devices, so the local identifier can be represented with fewer bits than a globally unique identifier, which speeds communication and saves electrical power consumed for communication purposes.

In some embodiments, the local device identifier may be stored in volatile or nonvolatile memory of the medical device. If stored in nonvolatile memory, the local identifier will be available again for use after reset or power-up of the medical device. A controller device is operable to identify each medical device upon power-up, assign a local identifier to each slave device, and communicate each local identifier to the associated slave device. The controller device may also command the local identifier to be written to nonvolatile memory prior to reset or power-up of the medical device.

An embodiment of a system includes multiple slave devices implanted in a human body, wherein each slave device includes a communication module operable to receive transmitted communications, and wherein each slave device is associated with a globally unique, or simply global, device identifier. The system further includes a master device including a communications module operable to address a first communication to a selected slave device using the global device identifier associated with the selected slave device, wherein the first communication includes a local identifier for assignment to the selected slave device, wherein the assigned local identifier does not match any other local identifier assigned to any other slave device implanted in that particular human body, and wherein subsequent communications are addressed to the selected slave device using the assigned local identifier.

An embodiment of a method includes assigning a local identifier to each of one or more of multiple slave medical devices, wherein each assigned local identifier is selectable during each communication session, transmitting a message to each of the one or more slave medical devices, wherein the message comprises the associated permanent device identifier and the assigned local identifier, and using the local identifier assigned to a selected one of the one or more slave medical devices to address subsequent communications to the selected slave device.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

Figure 1:
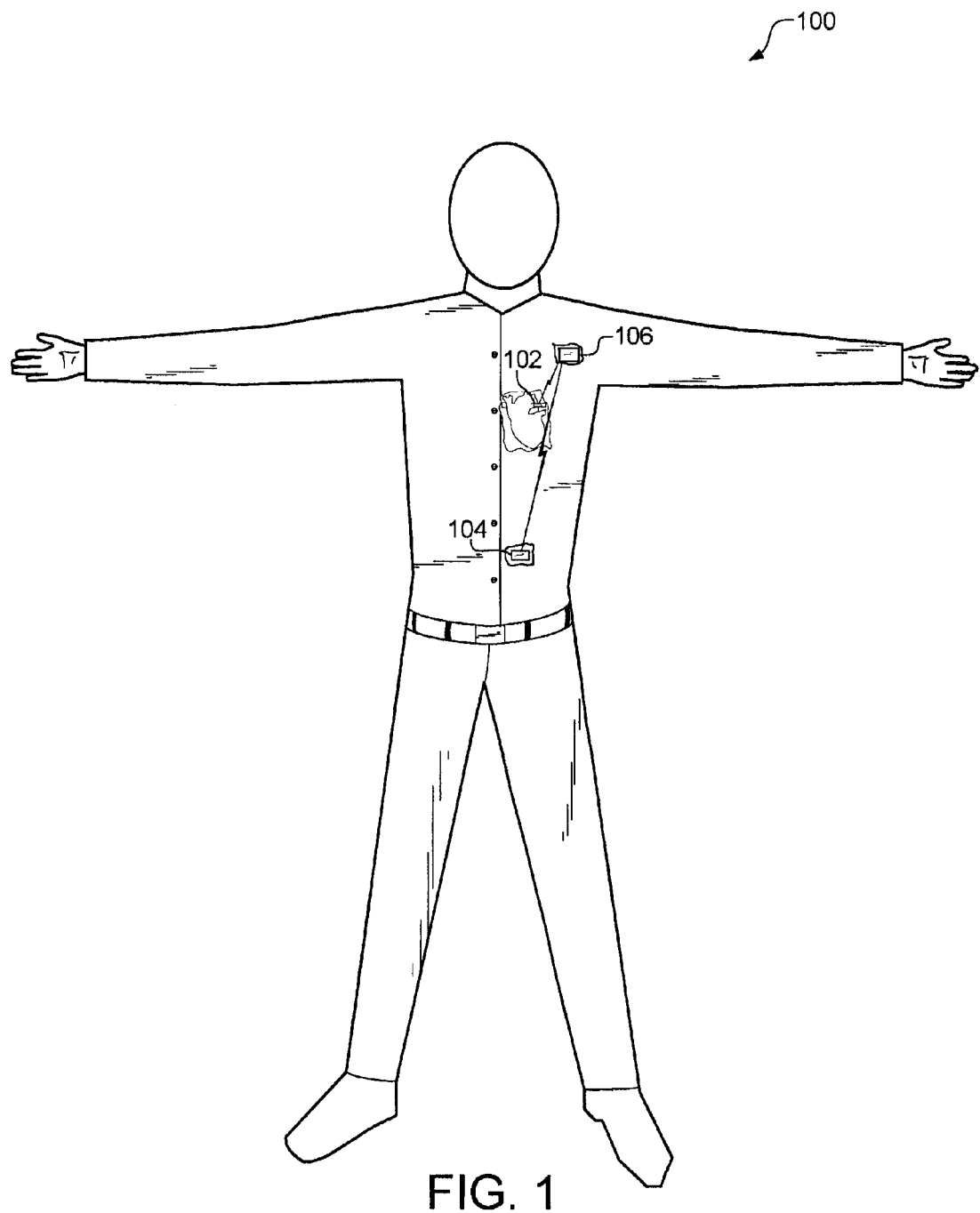
FIG. 1 illustrates a human patient with one or more slave implantable medical devices (IMD) in communication with a master device, wherein the slave devices are addressable using a local identifier.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable medical device (IMD) generally refers to any medical device that can be implanted in a human body to perform one or more of a sensing function or a therapeutic function. By way of example, but not limitation, an IMD may be operable to sense a physiologic parameter, such as blood pressure, temperature, posture, blood sugar level, or others. An IMD may be operable to provide therapy, such as, but not limited to, pulses for rhythm management in a patient's heart. In addition to sensing and therapy, an IMD may provide other functions, such as communications functions.

Embodiments described herein generally provide for communication between a master device and one or more implanted medical devices, which are configured as slave devices. The master device itself may also be implanted in the patient. More specifically, multiple implanted slave devices can be addressed by the master device. A local identifier is a locally unique address that is assigned to a slave device by the master device. For example, in a system of multiple slave devices implanted in a patient's body, each slave device can be assigned a local identifier that is locally unique to the slave device. The local identifiers can then be used by the master device to direct communications (e.g., commands or data) to the slave devices.

Advantageously, each local identifier is composed of substantially fewer bits than a conventional globally unique IMD identifier, such as a device serial number. In addition, the local identifier can be selected from one communication session to the next. As a result, the local identifier can be variable or static from one communication session to the next. By contrast, globally unique device identifiers, such as manufacturer's serial numbers, are permanent, and cannot change from one communication to the next. Permanent device identifiers, such as serial numbers, are also typically longer than the number of bits required to communicate with a comparably small number of devices in a local environment. A local identifier bit representation can be shorter, spanning only the number of unique devices likely to be implanted in any single human body.

For example, typically a device serial number is composed of twenty or more bits. Device serial numbers can be considered to be globally unique, because the likelihood of duplication of any one serial number is very small due to the length of the serial number. Although a slave IMD could be addressed using the slave's permanent device identifier, a local identifier requires fewer bits and can be variable. In one embodiment, local identifiers are composed of a number of bits sufficient to uniquely identify each of multiple slave IMDs implanted in a patient. As such, for example, but without limitation, a local identifier may require only between two and five bits to address each slave IMD within a patient.

In some embodiments each slave IMD executes a state machine that facilitates coordinated communication with the master device. According to one embodiment of a state machine, a slave device transitions from a reset state through an awake state to an eventual session state or suspend state, before returning to the reset state following communication session activity. In some embodiments, slave devices can also enter a charge state, in which a device battery is charged. The master device can cause a slave device to enter the awake state by sending a wakeup command to the slave device. A communication session between a master and a slave generally refers to a period of interaction that spans from the time the slave device wakes up until the slave device returns to the reset state. Using local identifiers, a master device can maintain simultaneous communication sessions with multiple slave devices. In some embodiments, data security is insured by including the local identifier in each command (master to slave) and each response (slave to master).

In accordance with some embodiments, the slave devices are configured to timeout after a specified time of no communication with the master device. In these embodiments, the master device can be configured to periodically establish (or reestablish) communications with the slave devices, in order to avoid timeout of the slave devices. In addition, one or more slave devices can be allowed to timeout, or the slave devices may be sent a command to cause the slave devices to enter a low power consumption state and/or a noncommunicative state.

Prior to describing specific embodiments in detail, some useful definitions are given. The term "address" is used as a verb or a noun in this specification, depending on the context. As a verb, the term "address" refers to the act of directing a communication to a medical device. Addressing a communication to a medical device may involve, for example, transmitting a message that includes a logical address or identifier associated with the medical device, such that the medical device recognizes the message as being directed at the medical device.

When the term "address" is used as a noun, "address" refers to a logical identifying location among one or more medical devices. An address is typically used to direct communications to a selected medical device. For example, a local address distinguishes a medical device in a system of medical devices, such that commands can be sent to a particular medical device. An identifier may be viewed as a type of address because an identifier can be used to direct a communication to an associated device.

The term "communication" refers to a set of data that can be transmitted or received. The set of data can be of any type. By way of example, but not limitation, a communication can refer to a message (e.g., a status message) or a command.

FIG. 1 illustrates a human body 100 with an IMD, such as a physiologic sensor device 102, implanted in a vessel of the circulatory system of the body 100, and another sensor device 104 located in an abdominal area of the human body 100. The sensor devices 102, 104 are operable to measure parameters, such as blood pressure, and blood glucose. Although two IMDs are illustrated in FIG. 1, in general, one or more IMDs can be implanted in the human body 100. A master device 106 is also implanted in the human body 100. The master device 106 is in communication with the sensor devices 102, 104.

More specifically, the master device 106 is configured to send commands to, and receive data from, the sensor devices 102, 104.

Accordingly, the sensor device 102 and sensor device 104 are examples of slave devices, because they respond to commands from the master device 106. The master device 106 may be a therapeutic or nontherapeutic device. Thus, the master device 106 may or may not include a sensor for performing sensory functions, and may or may not be operable to administer therapy to the patient 100.

FIG. 1 illustrates only one possible arrangement of the master device and slave devices. In an alternative embodiment, multiple slave devices can be attached to an anchoring mechanism at a single location in the body. For example, two sensor devices can be attached to a compressible retention device, and thereby anchored at a selected location. Particular embodiments of this type are shown and described in commonly owned and concurrently filed U.S. patent application Ser. No. 11/781,100, entitled "Multiple Sensor Deployment," claiming priority to U.S. Provisional Patent Application Ser. No. 60/820,050 and U.S. Provisional Patent Application Ser. No. 60/820,059, all of which are incorporated herein by reference in their entireties for all purposes.

Figure 2:
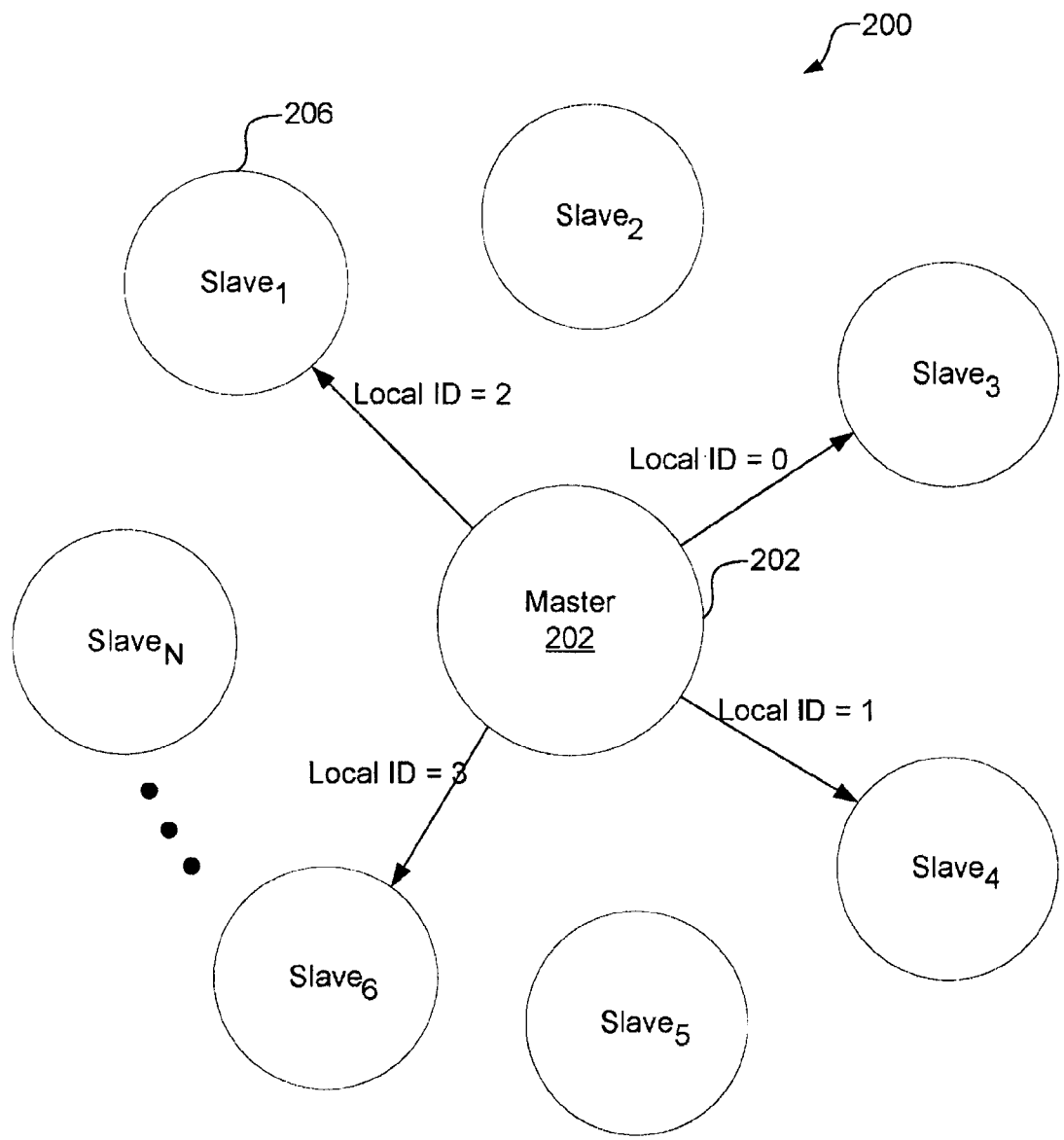
FIG. 2 is a schematic diagram illustrating a generalized system including a master device and one or more slave devices.

FIG. 2 is a schematic diagram 200 that more generally illustrates a system of medical devices including a master device 202 and one or more slave devices 206(n), wherein n ranges from one to M. Local identifiers are assigned and communicated to one or more of the slave devices 206(n). In the case of M less than or equal to eight, each local identifier can be composed of three bits. In the illustrated scenario, the master device 202 assigns local identifiers to slave devices 206(1), 206(3), 206(4), and 206(6). Although more than one slave device is illustrated in FIG. 2, it is to be understood that the processes described herein are applicable to a system that includes only one slave device.

Figure 3:
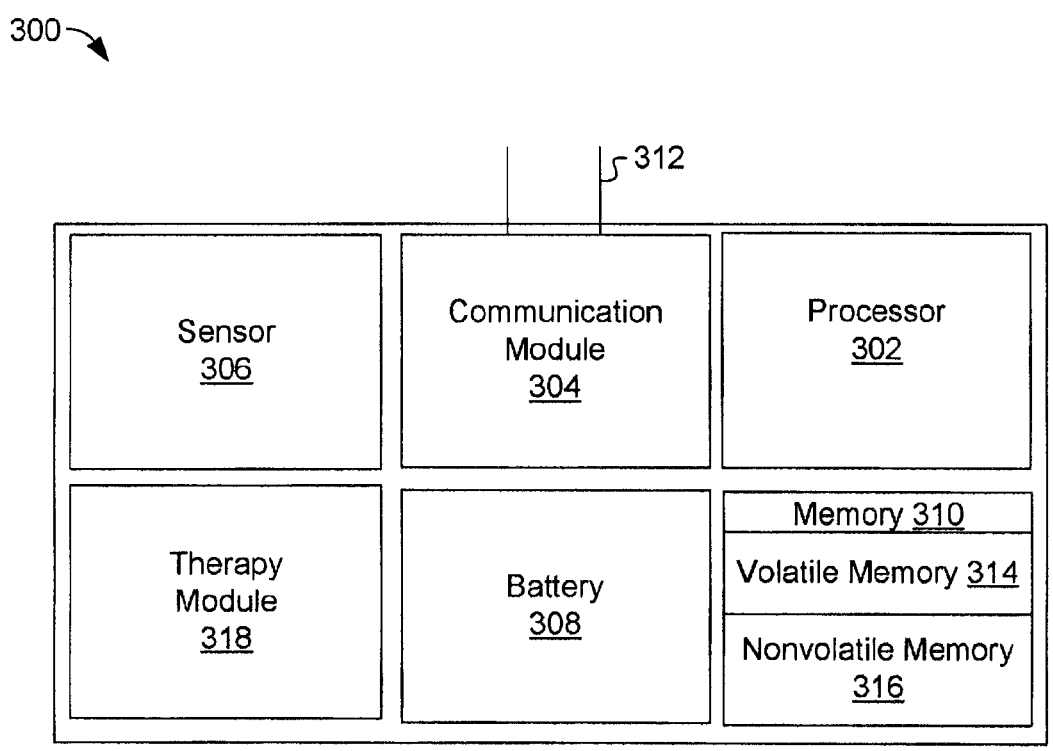
FIG. 3 is a functional block diagram illustrating functional components of a slave device in accordance with one embodiment.

FIG. 3 is a functional block diagram illustrating functional components of a slave device 300 in accordance with one embodiment. In accordance with various embodiments, the components of the slave device 300 are housed in a casing composed of a biocompatible material. In the embodiment of FIG. 3, the slave device 300 includes a processor 302, a communication module 304, a sensor 306 and/or a therapy module 318, a battery 308, and memory 310, which are in operable communication with each other (e.g., via a bus or circuit board traces).

Processor 302 may be any of a variety of processor as may be known in the art. By way of example, but not limitation, processor 302 may be a microprocessor, microcontroller, a digital signal processor, or application specific integrated circuit (ASIC). Typically, processor 302 has relatively low power requirements, and can implement basic processes, such as a simple state machine (e.g., state machine 500, FIG. 5).

Communication module 304 includes a receiver and transmitter (not shown) for communicating with another device, such as a master device. Preferably, the receiver and/or the transmitter can be disabled and enabled, depending on the state of the slave device 300. The communication module 304 can communicate using any of a variety of wired and/or wireless communication technologies, including, but not limited to, acoustic or radio frequency (RF). In some embodiments, communication module 304 is connected to leads 312, through which communication module 304 can communicate with another device, such as a master device. Of course, in a preferred embodiment, wireless communication is used, thereby obviating the need for leads 312. Sensor 306 is operable to sense a specified physiologic parameter, such as, but not limited to, blood pressure.

Memory 310 includes volatile memory 314 and nonvolatile memory 316. Volatile memory 314 is typically random access memory (RAM). In some embodiments, nonvolatile memory 316 includes electrically erasable programmable read only memory (EEPROM). Memory 308 can include processor 302 executable instructions to cause processor 302 to carry out a process. Battery 308 provides power to the components of the slave device 300. In some embodiments, battery 308 is rechargeable.

Figure 4:
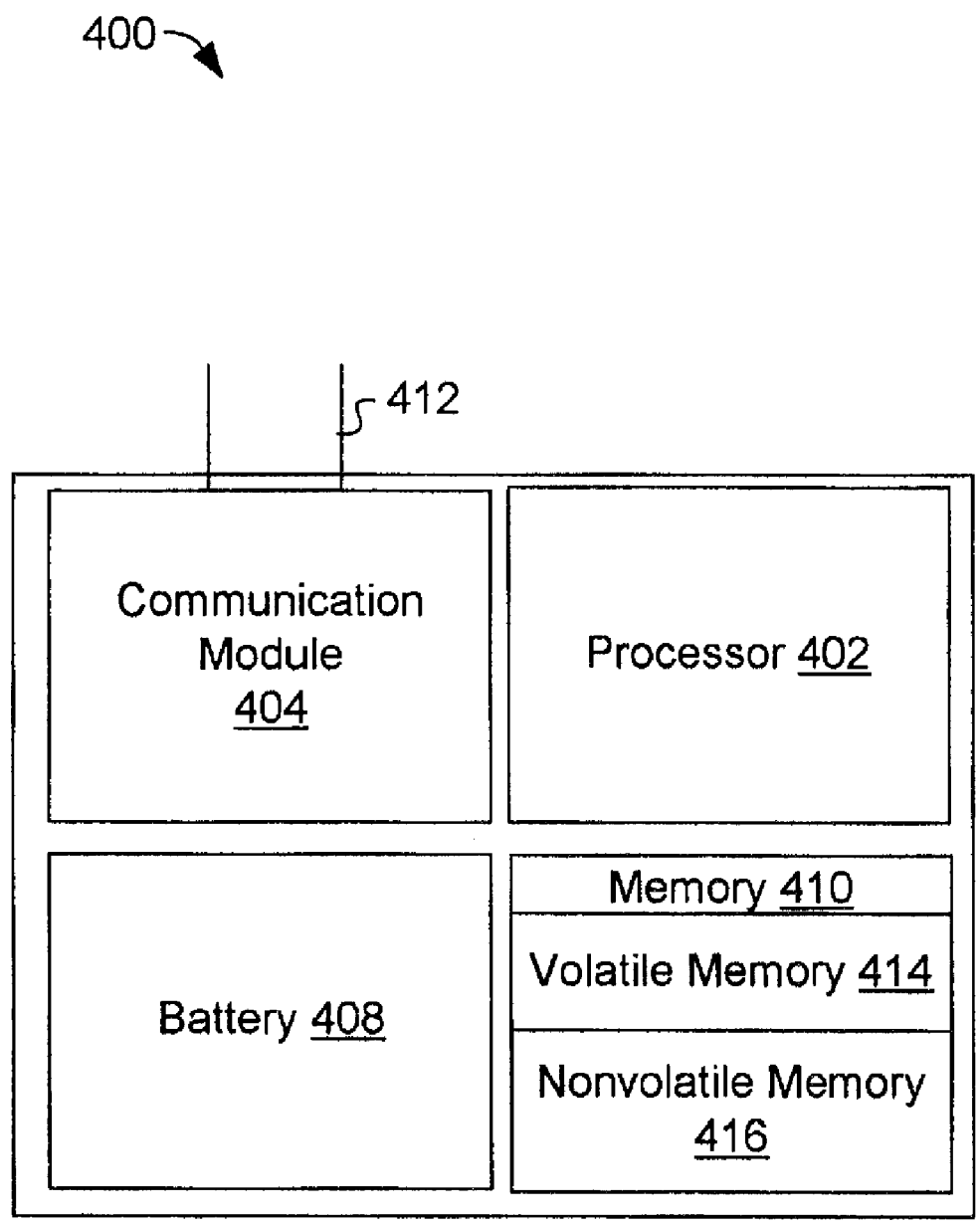
FIG. 4 is a functional block diagram illustrating functional components of a master device in accordance with one embodiment.

FIG. 4 is a functional block diagram illustrating functional components of a master device 400 in accordance with one embodiment. In accordance with embodiments in which the master device 400 is to be implanted in a patient, the components of the master device 400 are housed in a casing composed of a biocompatible material. In the embodiment of FIG. 4, the master device 400 includes a processor 402, a communication module 404, a battery 408, and memory 410, which are in operable communication with each other.

Processor 402 may be any of a variety of processor as may be known in the art. By way of example, but not limitation, processor 402 may be a microprocessor, microcontroller, a digital signal processor, or application specific integrated circuit (ASIC). Typically, processor 402 has relatively low power requirements, and can implement basic processes, such as the slave device management algorithm 700 shown in FIG. 7 and discussed below.

Communication module 404 includes a receiver and transmitter (not shown) for communicating with one or more slave devices. The communication module 404 can communicate using any of a variety of wired and/or wireless communication technologies, including, but not limited to acoustic or radio frequency (RF). In some embodiments, communication module 404 is connected to leads 412, through which communication module 404 can communicate via wire with one or more slave devices. Of course, a preferred embodiment of the communication module 404 communicates via wireless communication, which obviates the need for the optional leads 412.

As in the slave devices, memory 410 in the master device 400 can include volatile memory 414 and nonvolatile memory 416. Volatile memory 414 is typically random access memory (RAM). In some embodiments, nonvolatile memory 416 includes electrically erasable programmable read only memory (EEPROM). Memory 410 can include processor 402 executable instructions to cause processor 402 to carry out a process. Various data may be stored in nonvolatile memory 416. For example, prior to deployment, globally unique serial numbers of slave devices that the master device 400 will command, are stored in nonvolatile memory. Using the serial numbers, the master device 400 can initially address the slave devices. Battery 408 provides power to the components of the master device 400. In some embodiments, battery 408 is rechargeable.

Figure 5:
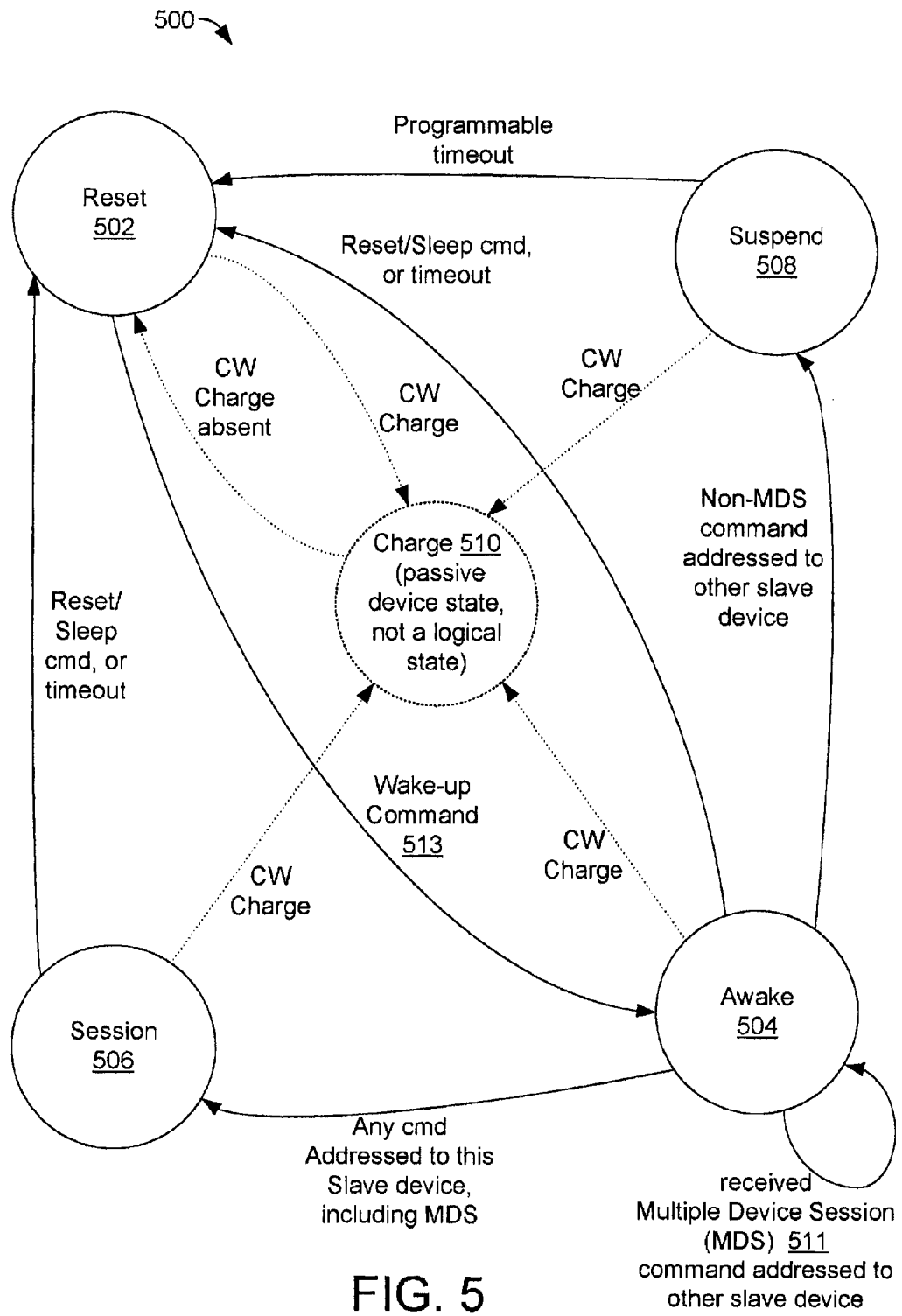
FIG. 5 is a state diagram illustrating a state machine that can be implemented by a slave device implanted in a patient, and in communication with a master device.

FIG. 5 is a state diagram illustrating a state machine 500 that can be implemented in a slave device implanted in a patient, and in communication with a master device. The state machine 500 includes a finite number of logical states, or modes, in which each of the slave machines can operate. At any particular time, the slave machines may be in the same or different states, depending on what commands or signals, if any, each of the slave machines has received from the master device. Prior to discussing each of the exemplary states in detail, exemplary commands are discussed, which can be issued by the master device, and can cause the slave devices to transition among the states.

In this particular embodiment, the master device is configured to generate commands for transmission to slave devices. All slaves recognize and react to a wake-up command 513 that a master employs to simultaneously transition all local devices into the Awake state 504. Two commands that transition individual slave devices to the Session state 506 or the Suspend state 508 are referred to here as, "Single Device Session" (SDS) 512, and "Multiple Device Session" (MDS) 511. In addition to wake-up and session commands, commands for master-to-slave interaction include data read and write commands, commands to prompt actions to be performed within individual slaves, and commands to transition slave devices to the Reset state 502.

In embodiments described herein, each slave device is configured to "timeout" and enter a nonresponsive or non-communicative, low power mode (referred to as a Suspend state 508, discussed below) if the slave device has not received a command within a predetermined length of time.

The identify (ID) command is used to identify a selected slave device among a plurality of slave devices, and cause the selected slave device to associate itself with an assigned local address or local identifier. In accordance with at least one embodiment, the ID command format includes a long identifier (e.g., 20-64 bits), such as a device serial number, which is permanent and globally unique, and a local address. The local address is a locally unique identifier that is represented with fewer bits than the long identifier. The term "locally unique" means unique among a set of slave devices implanted in, or otherwise carried by, a single patient. The local address can be dynamically assigned during a communication session, and therefore can be variable across communication sessions, or the local address can be static across communication sessions. In a set of multiple slave IMDs, some local addresses may be kept static (e.g., by writing them to non-volatile memory), while others may be allowed to change across communication sessions. The local address can be any number of bits in length, and in some embodiments ranges from two to five bits, depending on the number of slave devices in a medical device system implanted in a patient. For example, in some embodiments, each local address is composed of three bits, which allows for unique identification of up to seven slave devices.

After the master device uses the ID command to assign local addresses to one or more slave devices, the master device can use the local addresses to address commands to the slave devices, without using the globally unique long device identifier. Thus, commands discussed herein can be addressed to a selected slave device with the local address assigned to the selected slave device. The assigned local addresses may be used within a single communication session, and/or during subsequent communications sessions. In order to use an assigned local address in later sessions, the local address is stored in nonvolatile memory of a slave device so that the local address can be used when the slave device powers up later. In some embodiments, the master device controls whether and when local identifiers are stored to nonvolatile memory in the slave devices. After a local address is stored to nonvolatile memory, the local address will be available immediately upon exiting the Reset state 502, and the ID command with the globally unique identifier does not need to be used. In some embodiments, the slave device will also transmit the local identifier in all responses to the master device to insure integrity on all commands and responses.

Referring now to the state machine 500 of FIG. 5, the slave device starts in a Reset state 502. In a particular embodiment, the Reset state 502 is the default state because the slave device reverts to the Reset state 502 from other states under certain conditions. For example, when in either the Awake state 504 or the Session state 506, the slave device will transition to the Reset state 502 if a specified command is received. As another example, when in any of the Awake state 504, Suspend state 508, or Session state 506, the device transitions to the Reset state 502 after a finite time has passed and no command has been received from the master and the slave device has not transmitted any data. In short, devices can time-out and revert to the Reset state 502 from the other states.

In this particular embodiment, the Reset state 502 is a low power state, in which only certain components are enabled in order to reduce power consumption. For example, the slave device may have a receiver and minimal circuitry or processing components enabled to receive a signal from the master device. The slave device exits the Reset state 502 when it receives a "wake-up" signal or pulse from the master device. In one embodiment, the wake-up pulse is a signal that is broadcast by the master device and is recognized by each of the slave devices. Upon receiving a wake-up pulse from the master device, each slave device transitions into an Awake state 504.

In a particular embodiment of the Awake state 504, each slave device waits to be addressed by the master device. The master device follows the wake-up pulse with a command intended for a single slave device. The single slave device can be addressed at least in one of the following three ways:
 a globally unique slave device address, retained permanently within a slave from time of manufacture;
 a local device identifier, which was previously assigned; and
 a universal identifier, represented using the same number of bits as the local identifier.

With regard to the first item, a globally unique slave device address (e.g., a serial number) can be contained in an identification (ID) command that also includes an assigned local identifier that can be used later. A universal identifier is an address that is associated by default with all manufactured slave devices. All devices implanted within a patient are a subset of this population. As such, a slave device that receives a command addressed with the universal identifier will act on the command, unless the slave device has been assigned a different local identifier. As a result, when a command is sent with the universal identifier, more than one slave device could potentially act on the command.

A universal identifier can be used in cases when a slave device has not been assigned a particular local identifier. In accordance with at least one embodiment, the universal identifier is used when one and only one slave device is in a data transfer state (e.g., Awake state 504, or Session state 506) and all other devices are either not present within the body, or have been assigned a local identifier. A slave that transitions to the Session state 506 with the universal identifier may have restricted operations in the Session state 506. For example, writes to non-volatile memory may be blocked.

Continuing with the particular embodiment of FIG. 5, when a slave device is in the Awake state 504, and a local identifier has been assigned to it, commands from the master device are addressed to the slave device using the slave device's associated local identifier. Upon receipt of a command, each slave device determines validity of the command and whether the command is intended for that particular slave device. Validity can be based on a number of factors, such as, but not limited to, a cyclic redundancy check (CRC). The slave device checks the local identifier in the command to determine if the command is intended for it.

After a wake-up event from the Reset state 502, a slave device will stay in the Awake state 504 until a reset/sleep command is received, a timeout occurs, or a command is received that has a matching identifier (globally unique, local, or universal). A timeout is an interval of time ($T_{sleep}$) during which no master device commands have been received and the slave has not transmitted data.

When a device is in the Awake state 504, it waits for a command addressed to it, at which time the slave enters the Session state 506. If a command is received for which the address does not match and the command is not a Multiple Device Session command 511, the slave device enters a Suspend state 508. If a Multiple Device Session command is received that does not have a matching address, the slave device remains in the Awake state 504. If a command is received that has a matching address, the slave device enters the Session state 506.

In accordance with one embodiment, among others, the operation of a slave device is the same in the Session state 506 as it is in the Awake state 504, except that the slave device will not enter the Suspend state 508 directly from the Session state 506 when not addressed. The Session state 506 can be used by the master device to communicate with more than one slave device during a communication session. When a Multiple Device Session (MDS) command having an address of a selected slave device is received by the addressed slave, while in the Awake state 504, the selected slave device enters the Session state 506; but, the non-selected slave devices remain in the Awake state 504. As such, the master device can transmit multiple MDS commands to cause more than one slave device to enter the Session state 506.

In order to communicate with a single selected slave device during a communication session, the master initially sends any command other than the Multiple Device Session command with the local identifier of the selected slave, immediately following the wake-up command, when the slave devices are in the Awake state 504. In response, the other slave devices enter the Suspend state 508, while the selected slave device enters the Session state 506.

When a slave device is in Suspend state 508, the slave device will enter a very low current mode that blocks or blanks the input receiver. As a result, a slave device in Suspend state 508 cannot be addressed by the master device. After a programmable time interval, the slave device will re-enable the input receiver and enter the Reset state 502. In some embodiments, the programmable time interval ranges from 15 to 20 seconds; however, other time intervals may be used, depending on the particular implementation.

Various embodiments include a Charge state 510. The Charge state 510 is a passive state in which the slave device charges a battery. The Charge state 510 may be entered when the slave device detects a continuous wave (CW) signal that is recognized as a charge signal. The CW charge signal may be generated by the master device, or another device, such as a charger that is external to the patient's body. In the Charge state 510, the slave device can minimize power usage, for example, by disabling all the components except the components that are necessary for charging the battery. When the CW charge signal is no longer present, the slave device enters the Reset state 502.

Figure 6:
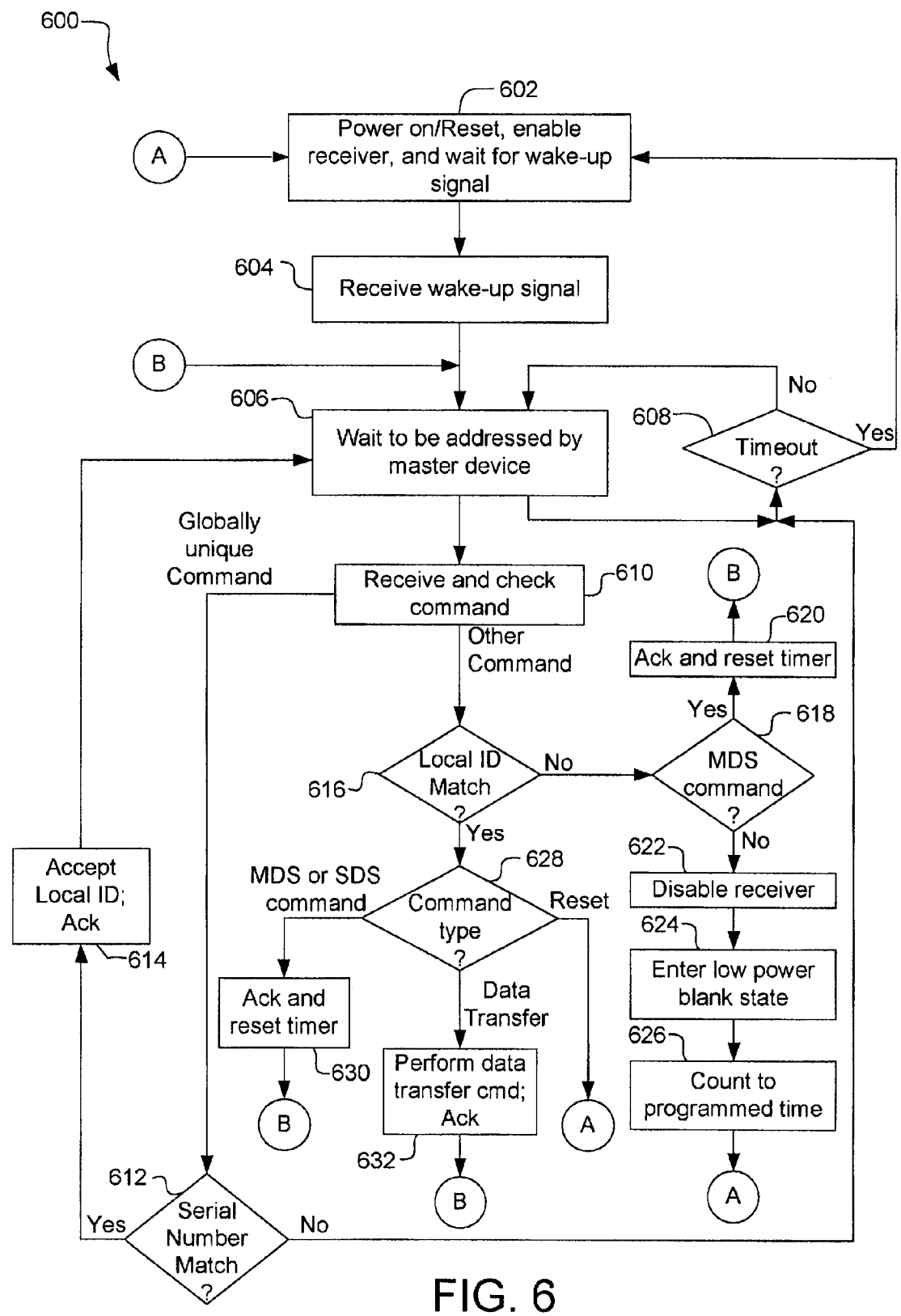
FIG. 6 is a flow chart illustrating an algorithm that can be carried out by a slave device that is in communication with a master device.

FIG. 6 is a flow chart illustrating an algorithm 600 that can be carried out by a slave device that is in communication with a master device. In various embodiments, whenever the slave device receives a command, the slave device performs certain validation operations to validate the command. In exemplary embodiments, validation may include performing a cyclic redundancy check (CRC) using a CRC value included in the command, and/or checking that a command type specified in the command corresponds to the format of the command. Those skilled in the art will appreciate how these validation operations can be performed, and thus, details of such validation operations are not described herein. In addition, for ease of illustration, it is assumed that the commands received by the slave device in the algorithm 600 are valid, but it should be understood that during actual operation received commands may not be valid for any number of reasons.

In a power-on operation 602, the slave device enables one or more components or portions of components in the slave device, increasing slave device power consumption, depending on the embodiment. In one embodiment, the receiver of a communication module is enabled to receive communications from the master device. After powering on, the slave device waits for a wake-up signal from the master device. In a receiving operation 604, the receiver receives the wake-up signal from the master device.

In a waiting operation 606, the slave device waits to be addressed by the master device. As discussed above, the slave device can be addressed in several ways: with a long device ID, a local identifier, or a universal identifier. The slave device is addressed with a command, such as one of the commands described above. The slave device also starts a timer counting for a specified time (e.g., $T_{timeout}$), which will be used to determine whether a timeout interval has passed. A query operation 608 determines whether the specified timeout time has passed. If the timeout time has not elapsed, the algorithm 600 branches "No" and returns to the waiting operation 606. If the timeout time has elapsed, the algorithm 600 branches "Yes" to the power on operation 602.

However, in another receiving operation 610, the slave device receives a command sent by the master device. When the slave device receives a command, the slave device checks the command type. If the command type is an identification command, the algorithm 600 branches "ID Command" to query operation 612. At query operation 612, the slave device determines whether the long device ID included in the ID command matches the slave device's permanent, globally unique identifier. If the global device IDs do match, the algorithm branches "Yes" to an accepting operation 614.

In accepting operation 614, the local identifier included in the command is saved in volatile memory and an acknowledgment response is transmitted to the master device. After the accepting operation 614, the algorithm returns to the waiting operation 606, resets the timeout timer, and awaits another command. If, however, the query operation 612 determines that the ID in the ID command does not match the slave device's global identifier, the algorithm 600 branches "No" to the query operation 608, and continues to count down from the timeout time.

If in the receiving operation 610 it is determined that the command is any type of command other than an ID command, the algorithm 600 takes branch "Other Command" to another query operation 616. In query operation 616, the slave device determines whether the local identifier of the command matches the local identifier of the slave device that received the command. If it is determined that the local identifier in the received command does not match the local identifier of the slave device, the algorithm 600 branches "No" to another query operation 618. In query operation 618, the slave device determines whether the command is a Multiple Device Session command.

If the command is a Multiple Device Session command, the algorithm branches "Yes" to acknowledging operation 620. Acknowledging operation 620 transmits an acknowledgment response and resets the timer. From the acknowledging operation 620, the algorithm 600 returns to the waiting operation 606 to await another command. In query operation 618, if the command is determined to not be a Multiple Device Session command, the algorithm branches "No" to a disabling operation 622. Disabling operation 622 disables the receiver of the slave device, so that the slave device will not receive communications from the master device. In an entering operation 624, the slave device then enters the Suspend state, in which power consumption is minimized. While in the Suspend state, the slave device performs a counting operation 626, in which the slave device counts for a specified length of time. After the counting operation 626, the algorithm returns to the reset state in the resetting operation 602.

Returning to the query operation 616, if it is determined that the local identifier of the command does match the local identifier of the slave device, the algorithm branches "Yes" to another query operation 628. The query operation 628 determines the command type. The command type can be determined by checking a command type field in the received command.

If the command type is a Single Device Session or Multiple Device Session command, the algorithm branches along the "MDS or SDS" path to an acknowledge (Ack) operation 630. In Ack operation 630, an acknowledgment response is issued and the timer is reset. After Ack operation 630, the algorithm returns to the waiting operation 606 to await another command. If, in the query operation 628, the command is determined to be another command type, the algorithm branches "Data Transfer" to a performing operation 632.

In performing operation 632, the slave device performs the specified command. For example, if the command is a read command, the slave device reads data from the requested memory location and transmits the contents of that memory location to the master device. If the command is a write command, the slave device writes the specified data to the specified location in memory and sends an acknowledgment response. If in the query operation 628, it is determined that the command is a Reset/Sleep command, the algorithm branches "Reset" and returns to the resetting operation 602.

Figure 7:
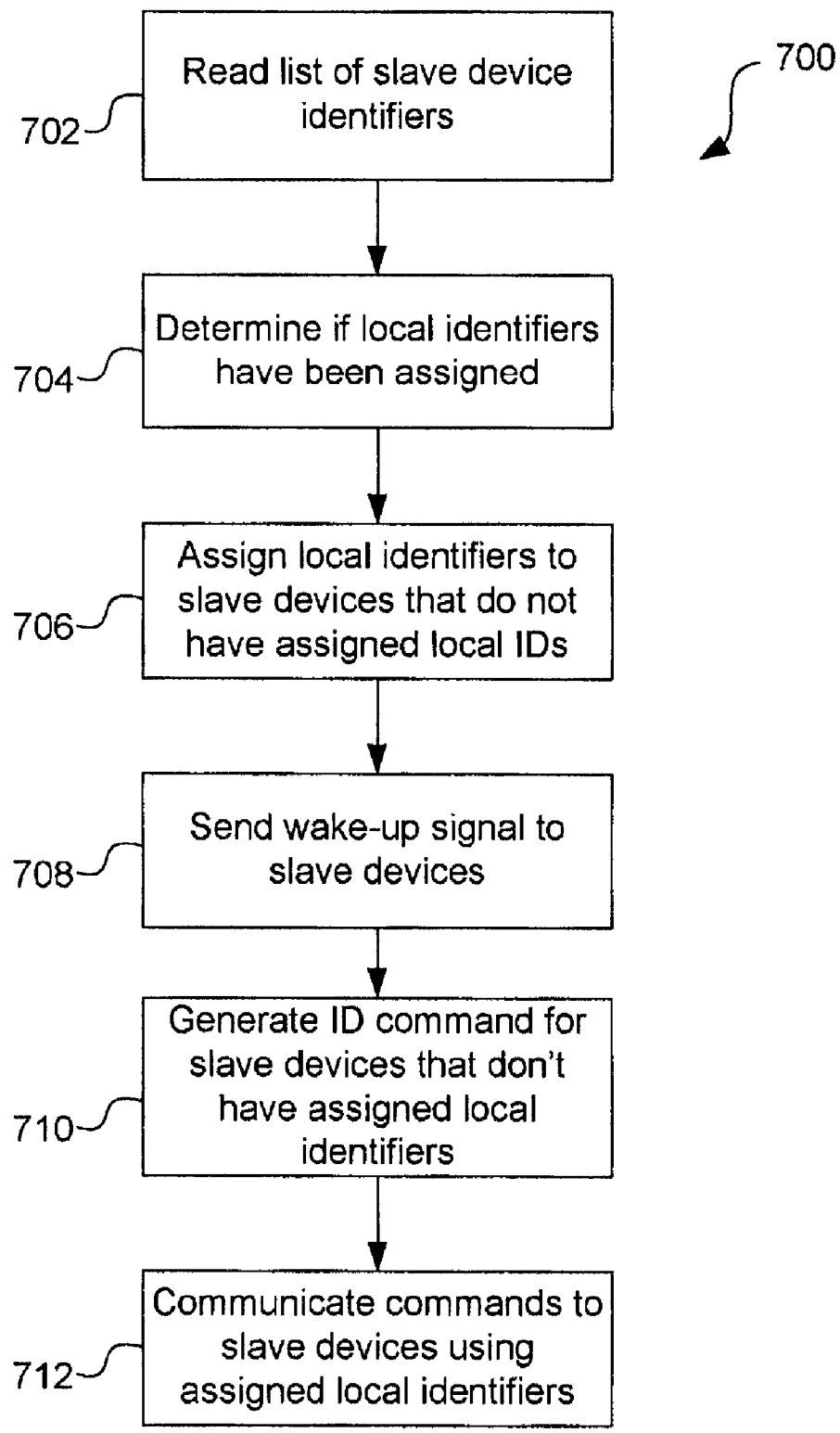
FIG. 7 is a flow chart illustrating an algorithm that can be carried out by a master device that is in communication with one or more devices.

FIG. 7 is a flow chart illustrating an algorithm 700 that can be carried out by a master device that is in communication with one or more slave devices in an implanted medical device system. In a reading operation 702, the master device reads one or more globally unique IDs associated with slave devices in the system. In a determining operation 704, the master device determines whether local identifiers have been assigned to one or more selected slave devices.

In an assigning operation 706, the master device assigns local identifiers to one or more selected slave devices. In a sending operation 708, the master device issues a wake-up signal to the slave devices, causing the slave devices to exit a low power reset state. In a generating operation 710, the master device generates one or more ID commands for one or more selected slave devices that do not have assigned local identifiers. In a communicating operation 712, the master device communicates the one or more ID commands to identify the slave devices and to transmit the assigned local identifiers. After the communicating operation 712, the master device may address future commands to selected slave devices using the local identifiers, without using the globally unique, long device ID. In some embodiments, the master device issues a subsequent command to instruct the slave devices to store the local identifier to a specified location in nonvolatile memory, so that the local identifier can be used in subsequent communication sessions.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system comprising:
a plurality of slave devices implanted in a human body, wherein each slave device includes a communication module operable to receive transmitted communications, and wherein each slave device is associated with a permanent device identifier;
a master device implanted in the human body, the master device including a communications module operable to address a first communication to a selected one of the slave devices using the permanent device identifier associated with the selected slave device, wherein the first communication includes a local identifier assigned to the selected slave device, wherein the assigned local identifier does not match any other local identifier assigned to any other slave device implanted in the human body, and wherein subsequent communications are addressed to the selected slave device using the assigned local identifier; and
wherein after a power reset of the selected slave device, the selected slave device is further operable to perform commands addressed to the selected slave device with the assigned local identifier, but that do not include the permanent device identifier of the selected slave device.

2. A system as recited in claim 1, wherein the assigned local identifier comprises a number of bits, and wherein the number of bits ranges from three to five bits.

3. A system as recited in claim 1, wherein the selected slave device includes volatile memory and nonvolatile memory, and wherein the selected slave device is operable to store the associated local identifier in volatile memory, and wherein the selected slave device is further operable to write the assigned local identifier to nonvolatile memory in response to a write command from the master device.

4. A system as recited in claim 1 wherein the device identifier is a manufacturer serial number.

5. A system as recited in claim 1 wherein the selected slave device is further operable to execute a state machine comprising an awake state, a reset state, and a suspend state, and wherein the selected slave device carries out a process comprising:
entering the reset state in response to a power on event;
entering the awake state upon receipt of a wake-up signal from the master device, wherein the selected slave device is operable to receive commands from the master device in the awake state;
entering the suspend state in response to receiving a command that is not a multiple device session command and that has a local identifier different from the local identifier assigned to the selected slave device, and wherein the selected slave device disables a receiver of the communication module upon entry into the suspend state, and returns to the reset state after a specified time.

6. A method for facilitating communication between a master device implanted in a body, and a plurality of slave medical devices implanted in the body, wherein each slave medical device has an associated permanent device identifier, wherein the method is carried out by the master device, the method comprising:
assigning a local identifier to each of one or more of the plurality of slave medical devices, wherein each assigned local identifier is selectable during each communication session, and wherein each local identifier comprises fewer bits than the permanent device identifier of the associated slave medical device;

transmitting a message to each of the one or more slave medical devices, wherein the message comprises the associated permanent device identifier and the assigned local identifier;

receiving an acknowledgment response from the selected slave medical device, the acknowledgment response indicating that the selected slave medical device has accepted the assigned local identifier; and using the local identifier assigned to a selected one of the one or more slave medical devices to address subsequent communications to the selected slave device.

7. A method as recited in claim 6 further comprising causing two or more of the plurality of slave medical devices to enter a multi-transfer state, wherein the master device is operable to transmit communications to the two or more slave medical devices using the respective local identifiers assigned to the two or more slave medical devices.

8. A method as recited in claim 6, further comprising determining that the selected one of the slave medical devices has timed out, after a specified time duration within which a response is not received from the selected one of the slave medical devices.

9. A method as recited in claim 6 further comprising sending a write command to the selected one of the slave medical devices, wherein the write command causes the selected one of the slave medical devices to store the assigned local identifier at a specified location in nonvolatile memory.

10. A method as recited in claim 9, wherein the specified location in nonvolatile memory is specified in the write command.

11. A method as recited in claim 6 further comprising:
sending a wake-up command to each of the slave medical devices when the devices are in a reset state;
sending a command to the selected slave medical device, wherein the command prevents the slave medical device from entering a noncommunicative state; and receiving an acknowledgment message from the selected slave medical device, wherein the acknowledgment message indicates that the slave medical device received the command.

12. A system comprising:
a plurality of slave medical devices implanted in a body, wherein each slave medical device includes a slave processing module and a slave communication module, and wherein each slave medical device is associated with a permanent device identifier that is globally unique, wherein each slave communication module is configured to receive transmitted communications; and a master device including a master processing module operable to assign a dynamically assigned local identifier to each of one or more associated slave medical devices among the plurality of slave medical devices, wherein each assigned local identifier is unique among the other assigned local identifiers and is shorter than the permanent device identifier, and wherein the master device further includes a master communication module configured to transmit each assigned local identifier to the associated slave medical device, and wherein the master communication module addresses subsequent communications to each of the one or more associated slave devices using the assigned local identifier, without using the associated global device identifier.

13. A system as recited in claim 12, wherein each slave medical device further includes volatile memory and nonvolatile memory, and wherein each slave processing module is operable to store a received local identifier in volatile memory, and await a write command from the master device before storing the local identifier in the nonvolatile memory.

14. A system as recited in claim 12 wherein the master module is configured to include an assigned local identifier in each command transmitted from the master device, wherein the assigned local identifier included in the command corresponds to the slave device to which the command is directed.

15. A system as recited in claim 12 wherein each slave device is configured to include the slave device's assigned local identifier in each response sent from the slave device.

* * * * *